US007662994B2

United States Patent
Makovec et al.

(10) Patent No.: US 7,662,994 B2
(45) Date of Patent: Feb. 16, 2010

(54) METHOD FOR THE PREPARATION OF CRYSTALLINE DEXLOXIGLUMIDE AND PRODUCTS OBTAINED

(75) Inventors: Francesco Makovec, Lesmo (IT); Lucio Claudio Rovati, Monza (IT)

(73) Assignee: Rottapharm S.p.A., Milan (IT)

( * ) Notice: Subject to any disclaimer, the term of this patent is extended or adjusted under 35 U.S.C. 154(b) by 83 days.

(21) Appl. No.: 10/562,013

(22) PCT Filed: Jun. 21, 2004

(86) PCT No.: PCT/IB2004/002208

§ 371 (c)(1),
(2), (4) Date: Dec. 23, 2005

(87) PCT Pub. No.: WO2004/113271

PCT Pub. Date: Dec. 29, 2004

(65) Prior Publication Data

US 2006/0154987 A1    Jul. 13, 2006

(30) Foreign Application Priority Data

Jun. 23, 2003    (IT)    ............................ TO2003A0474

(51) Int. Cl.
    *C07C 229/00*    (2006.01)
(52) U.S. Cl. ........................ 562/448; 562/449; 562/450
(58) Field of Classification Search ................. 562/448, 562/449, 450
    See application file for complete search history.

(56) References Cited

U.S. PATENT DOCUMENTS

| 5,130,474 A * | 7/1992 | Makovec et al. ............. 562/448 |
| 5,314,506 A * | 5/1994 | Midler et al. ............. 23/295 R |
| 5,602,179 A | 2/1997 | Makovec et al. |
| 7,122,083 B2 * | 10/2006 | Green ........................ 117/68 |

OTHER PUBLICATIONS

Database CA 'Online! Chemical Abstracts Service, Columbus, Ohio, US; Martin Katschinski: "Loxiglumide. Rotta Research", XP002306781, retrieved form STN Databse accession No. 2002: 580170 abstract & IDRUGS, 5(5), 469-474 CODEN: IDRUFN; ISSN: 1369-7056, 2002.
Database CA 'Online! Chemical Abstracts Service, Columbus, Ohio, US; Gabro Vargas: "DexIoxiglumide. (Rotta Research Lab)", XP002306782, retrieved form STN Databse accession No. 2002: 580010 abstract & Current Opinion in Investigational Drugs, 3(4), 621-626 Coden: COIDAZ; ISSN: 1472-4472, 2002.
Database CA 'Online! Chemical Abstracts Service, Columbus, Ohio, US; M. Fried, et al.: "The Role of Fat and Cholecystokinin in Functional dyspepsia", XP002306783, retrieved form STN Databse accession No. 2002: 577063 abstract & GUT, 51(Suppl. 1), 154-157 CODEN: GUTTAK; ISSN: 0017-5749, 2002.
Database CA 'Online! Chemical Abstracts Service, Columbus, Ohio, US; S. Persiani, et al.: "Pharmacokinetics of DexIoxiglumide after Administration of single and repeat oral escalating doses in healthy young males", XP002306784, retrieved form STN Databse accession No. 2002: 485631 abstract & International Journal of Clinical Pharmacology and Therapeutics, 40(5), 198-206 CODEN: ICTHEK; ISSN: 0946-1965, 2002.
Database CA 'Online! Chemical Abstracts Service, Columbus, Ohio, US; M. Maselli, et al.: "Effect of three nonpeptide Cholecystokinin antagonists on human isolated gallbladder", XP002306785, retrieved form STN Databse accession No. 2002: 50662 abstract & Digestive Diseases and Sciences, 46(12), 1773-2778 CODEN: DDSCDJ; ISSN: 0163-2116, 2001.
Database CA 'Online! Chemical Abstracts Service, Columbus, Ohio, US; Laura Revel, et al.: "DexIoxiglumide: CCK1 (CCKA) receptor antagonish treatment of irritable bowel syndrome", XP002306939, retrieved form STN Databse accession No. 1999: 656782 abstract & Drugs of the Future, 24(7), 725-728 CODEN: DRFUD4; ISSN: 0377-8282, 1999.
Database CA 'Online! Chemical Abstracts Service, Columbus, Ohio, US; Gabor Varga, et al.: "Different form actions of CCK on pancreatic and gastric growth in the rat: effect of CCKA receptor blockade":, XP002306940, retrieved fo STN Databse accession No. 1998: 370098 abstract & British Journal of Pharmacology, 124(3), 435-440 CODEN: BJPCBM; ISSN: 0007-1188, 1998.
Database CA 'Online! Chemical Abstracts Service, Columbus, Ohio, US; C. Scarpignato, et al.: "Effect of DexIoxiglumide and spiroglumide, two new CCK-receptor antagonists, on gastric emptying and secretion in the rat: Evaluation of their receptor selectively in vivo", XP002306786, retrieved form STN Databse accession No. 1996 398396 abstract & Alimentary Pharmacology, 10(3), 411-419 CODEN: APTHEN; ISSN: 0629-2813, 1996.

* cited by examiner

*Primary Examiner*—Daniel M Sullivan
*Assistant Examiner*—Sudhakar Katakam
(74) *Attorney, Agent, or Firm*—Sughrue Mion, PLLC

(57) ABSTRACT

The present invention describes a novel method for the purification of dexloxiglumide by crystallization from isopropyl ether which permits the production, in a reproducible manner, of a product with morphological and particle-size characteristics such as to favor its use in the preparation of oral pharmaceutical forms on an industrial scale.

13 Claims, 4 Drawing Sheets

(dexloxiglumide – Lot   PP9282/43851)

(dexloxiglumide – Lot  G3919/43781)

METHOD FOR THE PREPARATION OF CRYSTALLINE DEXLOXIGLUMIDE AND PRODUCTS OBTAINED

This is a National Stage entry of International Application PCT/IB2004/002208, with an international filing date of Jun. 21, 2004, which was published as WO 2004/113271 A3, and the complete disclosure of which is incorporated into this application by reference.

BACKGROUND OF THE INVENTION

The subject of the present invention is a novel method for the preparation, by crystallization from isopropyl ether, of (R)-4-[(3,4-dichlorobenzoyl)amino]-5-[(3-methoxypropyl)-pentylamino]-5-oxo-pentanoic acid (dexloxiglumide, CR 2017); molecular formula: $C_{21}H_{30}Cl_2N_2O_5$; CAS Registry Number: 119818-90-2.

Dexloxiglumide, the compound which is the subject of the present invention, has been shown to possess potent antagonistic activity towards the type-1 cholecystokinin ($CCK_1$) receptor. Dexloxiglumide can therefore be used advantageously for the treatment of various diseases in man, such as some pathological conditions of the gastrointestinal tract, for example, irritable colon syndrome, non-ulcerative dyspepsia, biliary colic and dyskinesia, gastro-oesophageal reflux, pancreatitis or, more generally, gastrointestinal motility disorders.

The preparation and some pharmacological activities of this compound have already been described, for example, in U.S. Pat. No. 5,602,179.

The final purification of the product was performed by crystallization from an $H_2O$/alcohol mixture in the ratio of 2:1 (v/v). This purification enabled a chemically pure compound, that is, with a chemical purity and an optical purity greater than 99.5%, to be obtained.

However, the rheological characteristics of the product thus obtained where wholly unsatisfactory since the crystal had poor flowability properties, preventing its advantageous use for the preparation of oral pharmaceutical forms such as, for example, tablets.

Moreover, trying to vary the relative proportions of the two components of the aqueous/alcoholic mixture did not improve the characteristics of the raw material which, on the contrary, still had mixtures of polymorphs.

SUMMARY OF THE INVENTION

A first object of the invention is to provide a method which permits the production of a crystalline product which is free of polymorphic forms and which has a crystalline form and a distribution of particle sizes having the desired physical properties suitable for the preparation of pharmaceutical forms for oral use on an industrial scale.

A particular object of the invention is to provide a method which can produce crystalline dexloxiglumide having flowability characteristics suitable for the formulation of tablets.

Flowability is perhaps the most important of the physical properties of any powder which is intended for use in tablet formulations. Poor flowability in fact means that the powder will be difficult to handle, tending to stick to the various surfaces that are in contact with the materials, thus causing problems in the supply to the metering and compression chambers of the presses.

This often occurs when an uncontrolled crystallization process produces crystals of greatly differing shapes and sizes in which smaller crystals of more or less differing shapes accumulate unevenly on the larger crystals. The distribution of the particle sizes is generally polymodal in these cases and it is thus difficult to obtain a product having a specific and reproducible distribution of particle sizes.

It is therefore important, from the point of view of an industrial process, to obtain a product in which, once an optimal distribution of size and crystalline shape has been identified, these remain constant and reproducible.

Another object of the invention is to provide a method which enables a Gaussian or unimodal distribution of particle sizes to be obtained, or even a bimodal distribution in which the peak corresponding to the quantitatively smaller distribution does not exceed 10-15% by weight of the total.

In view of the above-mentioned objects, the subject of the invention is a method as defined in the appended claims.

A crystalline powder and pharmaceutical compositions for oral use comprising the powder are also subjects of the invention.

Once the crystallization solvent of choice had been identified, in this case isopropyl ether, which enabled a powder with a high degree of purity, high crystallization yield, ease of drying, and with a pure crystalline form free of polymorphic forms to be obtained, numerous experiments were performed in order to identify the ideal crystallization conditions which would permit the preparation, where possible, of a powder having a morphology and a particle size such as to give it flowability and compressibility characteristics suitable for use with rotary presses.

It was also found that, in order for this product to possess good flowability characteristics, the level of fine particles (<10 μm) had to be limited and in any case no greater than 15%.

In order to try to obtain a powder which was suitable for compression with regard both to morphology and to particle size, numerous parameters were evaluated and optimized; these were, for example, the optimal solute/solvent ratio, that is, the dexloxiglumide/isopropyl ether ratio, the quality and quantity of the seeding material, taking into account that the seeding material should have a sufficiently fine grain size so that the seeding surface area was large relative to the total mass, the temperature at which the seeding material was added to the supersaturated solution of the crude product, and the curve of the rate of cooling of the system.

As stated above, the product obtained as described in U.S. Pat. No. 5,602,179, that is, by final purification with an aqueous/alcoholic mixture, had unfavourable rheological characteristics.

The techniques which are generally used to characterize the principal rheological properties of a powder for use in the preparation of oral pharmaceutical forms are:

a) measurement of the compressibility of the powder which is expressed by the following formula (Carr index; (according to USP 24/NF19, p. 1914):

$$\text{Compressibility index} = \frac{100(V_o - V_f)}{V_o}$$

where $V_o$ and $V_f$ are respectively the volumes occupied by a predetermined weighed quantity of powder (generally 100 g) placed in a 250 ml graduated cylinder and measured before and after a certain number of mechanical strokes (generally 2000 strokes); the smaller this index is the better will be the behaviour of the powder upon compression; for example, percentage values between 5-15 are considered excellent, whereas values greater than 33 are considered very poor (see J. I. Wells—Pharmaceutical Preformulation; Ellis H. Lim; J. Wiley and Sons Ed. p. 210);

b) measurement of the particle size distribution (PSD); it should be noted that the PSD not only affects the flowability of the powder and hence its pharmaceutical use, but also has an important role in the dissolving rate of the active ingredient, and hence in its bio-availability, and therefore in the efficacy of the active ingredient.

The PSD is determined by the "laser light scattering" technique, that is, the scattering (diffraction) which a high-energy, monochromatic light beam (a laser beam) undergoes when it encounters a particle of a particular size on its optical path.

The powder to be examined may be prepared by various techniques, both dry and wet; in the latter case, the selection of the dispersant should take account of the chemical/physical properties of the raw material to be analyzed. Once the sample has been analyzed, the results can be given as histograms in which each individual column represents a band of a certain width (in microns), whereas the height represents the percentage of sample present in that band.

The principal statistical distribution values calculated by the software of this apparatus are, amongst other things, the $D_{50}$, that is, the size in microns for which 50% of the sample is smaller and 50% is larger. Another important measurement is the "span", which is the measurement of the width of the distribution.

This width is calculated by the following ratio:

$$\frac{D_{90} - D_{10}}{D_{50}}$$

where $D_{90}$ and $D_{10}$ have meanings analogous to that of $D_{50}$. The smaller this "span" index is, the more reliable the particle distribution of the sample examined will be.

The dexloxiglumide obtained by crystallization from $H_2O$/ethanol (2:1 v/v) had a Carr index >33 and hence a very poor expected flowability. Moreover, its particle distribution had a bimodal shape with a $D_{50}$ value of 23.6 µm, the percentage of particles <10 µm was 29.5% and the span index was 4.668, that is, with a very wide distribution curve.

As expected, the powder obtained with these rheological characteristics was wholly unsuitable for the preparation of a pharmaceutical product in tablet form.

Attempts to change the relative percentage of the aqueous/alcoholic components were unsuccessful as was the selection of other solvents miscible with $H_2O$. Amongst the organic solvents which are immiscible with $H_2O$, solely the use of isopropyl ether and the particular crystallization method described in detail below enabled the problem to be solved.

The use of isopropyl ether as crystallization solvent, together with the method used, afforded the following advantages:

a) a high crystallization yield, b) low solvent usage (solvent/solute ratio of between 1.5:1 and 3:1 volume/weight);

c) ease of drying, d) lack of polymorphic forms in the crystallized product, e) favourable rheological characteristics.

Amongst the various crystallization tests which were carried out with isopropyl ether in order to optimize the production method, the following method, performed on a mass of 44 kg of crude product, is described by way of example.

DETAILED DESCRIPTION OF THE INVENTION

Example 1

Figure 1A:
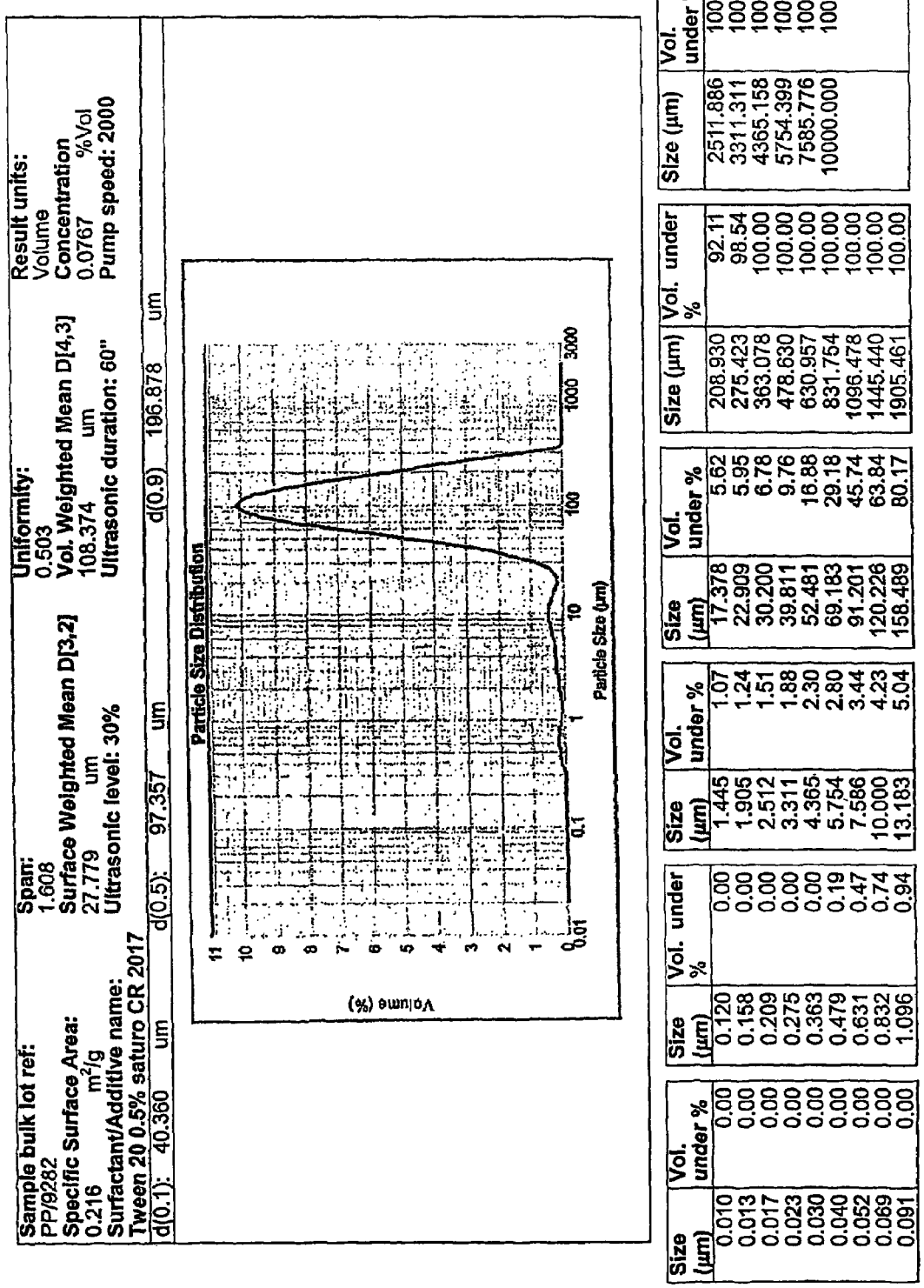
FIGS. 1A and 1B are particle distribution curves of a lot of dexloxiglumide prepared in accordance with the prior art (FIG. 1B) and in accordance with the method of the invention (FIG. 1A)

44 kg of crude dexloxiglumide was suspended in 100 liters of isopropyl ether in an enamelled 400 liter reactor and heated with stirring until the mass was brought to about 55° C. and a clear solution was obtained. The solution thus obtained was cooled, still with stirring, until it was brought to the metastable supersaturation zone at about 36-38° C.

At this point, 800 g of seeding material (ground dexloxiglumide with $D_{50}$ of about 20 µm) was added and the temperature of the mass was kept constant at 35-36° C. for 4 h. A cooling ramp was then imposed and brought the reaction mass to 6° C. over a period of about 8 h. The precipitate thus formed was filtered and dried to give 43 kg of product with a yield of 96% (also calculating the seeding material).

The crystalline product thus obtained (lot PP9282/43851) had a Carr index of about 12 thus predicting good flowability.

The apparatus used for the determination of the PSD was a Malvern Master Sizer 2000 and the method used was the wet method with the use of $H_2O$ as the dispersant with a concentration of 0.5% of Tween 20 as surfactant.

The measurements were taken at a concentration of dexloxiglumide of about 0.06-0.08% after ultrasound sonication for 60 sec which enabled the accumulations to be broken up without breaking the crystals.

The particle-size analysis was in line with the Carr index. The distribution was practically unimodal; the mean size measurement ($D_{50}$) was 97.3 µm, the percentage of fine particles (10 µm) was 4.23%, and the span index was 1.608 and hence with a fairly narrow particle distribution.

Figure 1B:
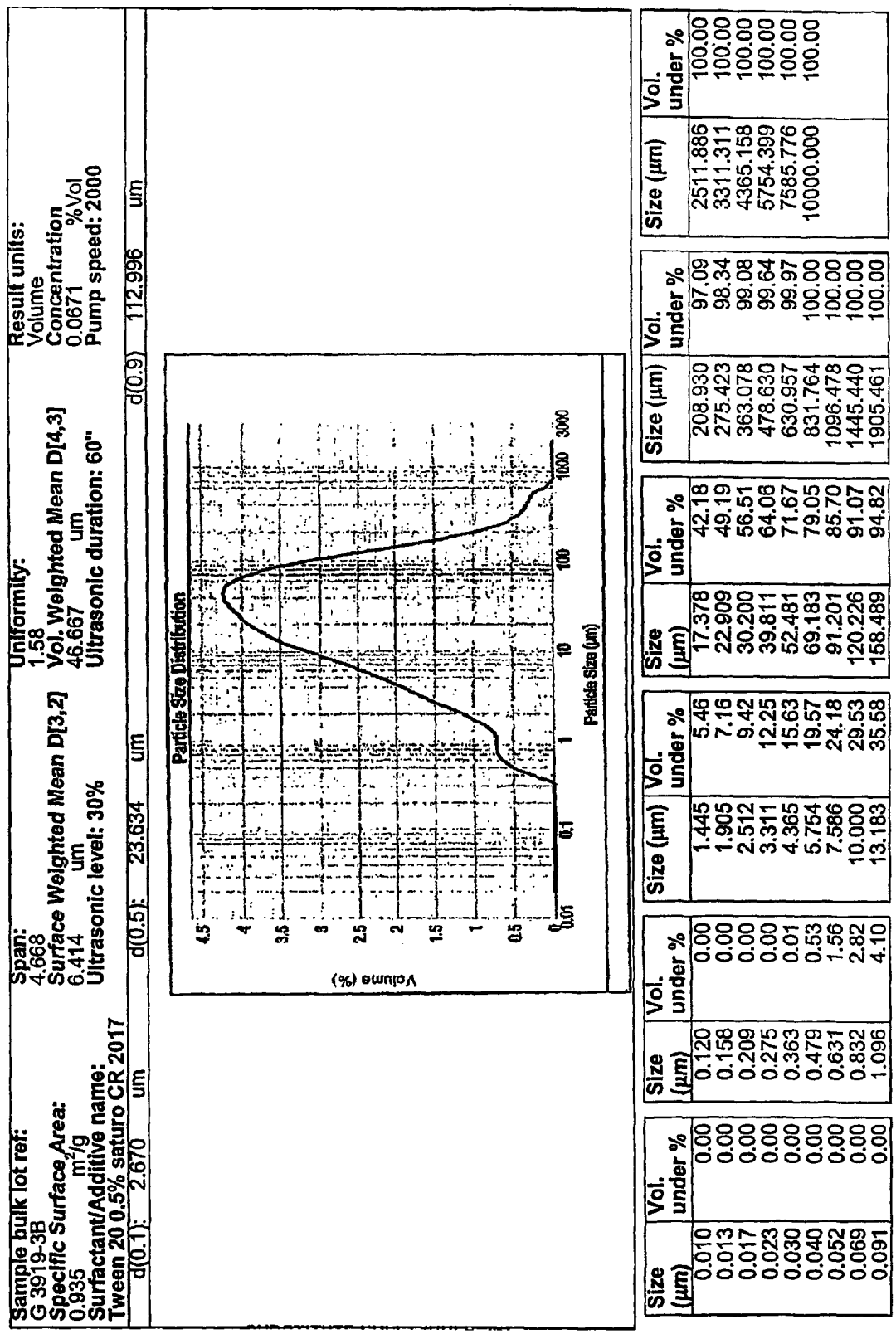

In FIG. 1, the particle distribution curve of a lot of dexloxiglumide prepared by crystallization from ethanol/$H_2O$ (lot G3919-3B) is compared with that of lot PP9282 which was crystallized from isopropyl ether as described in Example 1; the parameters indicated above, amongst others, are given in FIG. 1.

Morphological analysis performed by microscopic analysis of the crystals obtained by crystallization from ethanol/$H_2O$ and isopropyl ether, respectively, also confirms what had already been seen with by particle-size analysis by laser-beam diffraction.

Figure 2A:
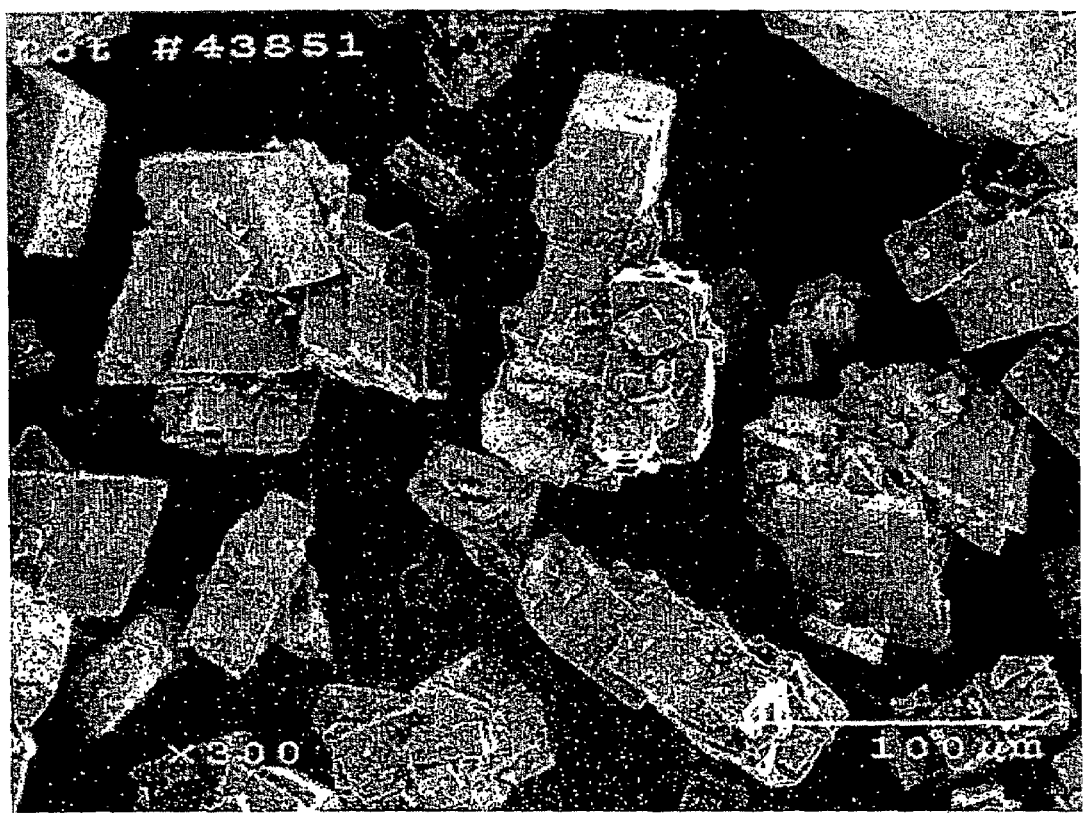
FIGS. 2A and 2B are photographs taken with 300× magnification of a dexioxiglumide sample prepared in accordance with the method of the invention (FIG. 2A) and of a sample crystallized from aqueous/alcoholic solvent in accordance with the prior art (FIG. 2B), respectively.
Figure 2B:
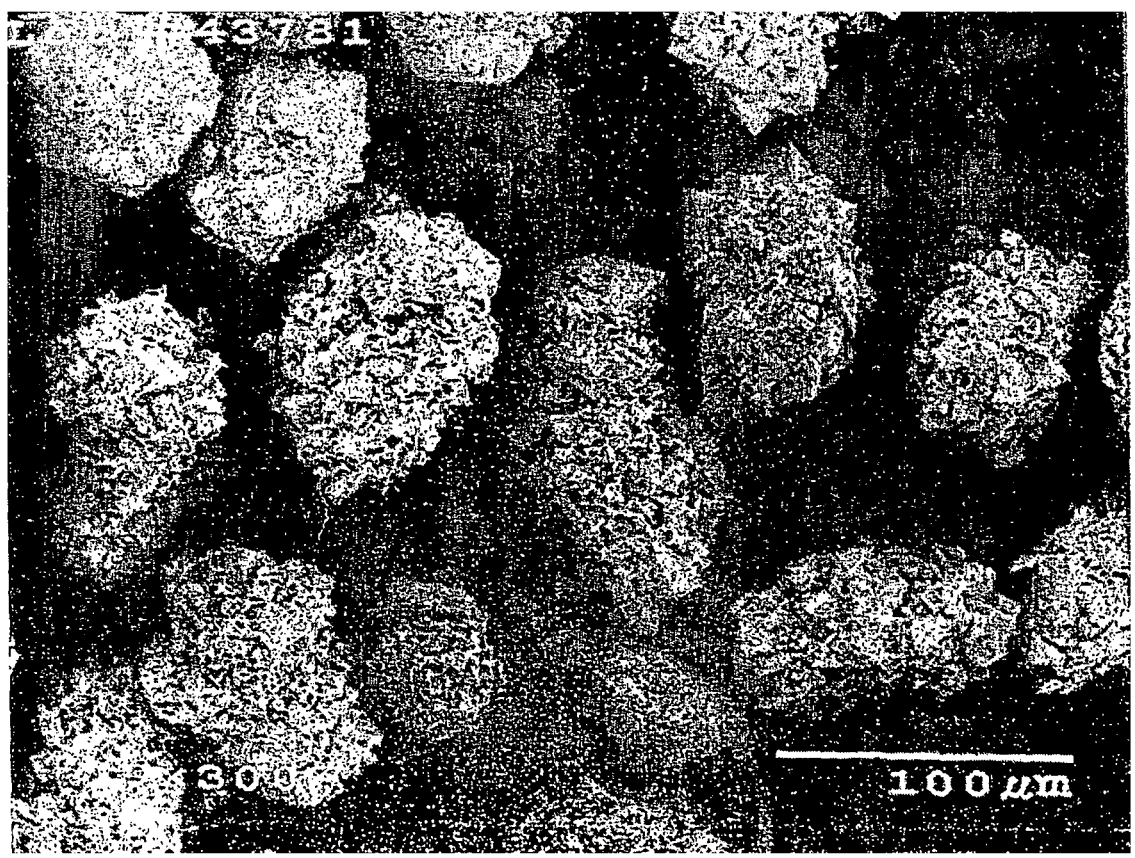

FIG. 2 shows photographs taken with 300× magnification of a sample of dexloxiglumide lot PP9282/43851 prepared in accordance with the method of the invention (FIG. 2A) in comparison with a sample obtained conventionally with the use of aqueous/alcoholic solvent (FIG. 2B).

It can be seen from a comparison of the two images of FIG. 2 that the product crystallized from isopropyl ether has crystals with well-defined, lamellar shapes with an average diameter of about 70-100 µm, whereas the other lot has crystals of irregular shape with very many smaller aggregated crystals.

The dexloxiglumide lot PP9282/43851 which was prepared in accordance with the invention was used to prepare tablets containing 200 mg of active ingredient for an overall unitary weight of about 440 mg, with the use as excipients, of cellulose (diluent), starch, sodium glycolate (disaggregant), talc, magnesium stearate, and silicon dioxide (lubricants).

About 200,000 tablets were prepared without flowability problems, thus ensuring a uniform supply to the compression chambers without problems of sticking to the metal surfaces or problems of uniformity of content of the tablets.

Bio-availability tests in vitro carried out by the dissolution test in accordance with the USP, method 2 (Paddle), with the use of 900 ml of pH 7.4 (0.05 M) phosphate buffer as dispersant at 37° C. and 50 rpm were also positive since more than 85% of the active ingredient dissolved rapidly within 30 minutes.

In conclusion, the novel method for the preparation of dexloxiglumide by crystallization from isopropyl ether according to the invention has permitted the production of a product which is suitable for the industrial preparation of oral pharmaceutical forms in the form of tablets, which are otherwise impossible to produce on an industrial scale.

Note: The particle sizes given both in the text and in the claims are not absolute quantities but are relative to the measurement method used (in this case the Malvern Master Sizer 2000 instrument with the method described in Example 1).

The invention claimed is:

1. A method for the preparation of crystalline dexloxiglumide by crystallization of the crude product from solvent, characterized in that isopropyl ether is used as solvent, wherein the crystallization step is performed by adding a seeding of microcrystalline dexloxiglumide having an average particle size $(D_{50}) \leqq 20$ µm to a supersaturated solution of crude dexloxiglumide;

wherein the dexloxiglumide is in crystalline particle form having a percentage by volume of less than 15% of fine particles having dimensions less than 10 µm, and an average particle size value $(D_{50})$ of between 50 and 130 µm.

2. A method according to claim 1, characterized in that a ratio of one part by weight of crude product with a quantity of between 1.5 and 3 parts by volume of isopropyl ether solvent is used.

3. A method according to claim 1, characterized in that the seeding is added to a supersaturated solution of crude dexloxiglumide which is kept at a temperature of between 35 and 40° C., in a ratio of one part of seeding material to 40-200 parts of crude product.

4. A method according to claim 1, wherein after the addition of the seeding material, the reaction mass is stirred at a temperature of from 34 to 38° C. for a period of from 2 to 8 h, and the temperature of the reaction mass is then reduced slowly, with stirring, to 10±5° C. over a period of from 6 to 10 h, and wherein the crystallized solid is recovered by filtration.

5. Dexloxiglumide in crystalline particle form having a percentage (by volume) of less than 15% of fine particles having dimensions less than 10 µm, and an average particle size value $(D_{50})$ of between 50 and 130 µm.

6. Dexloxiglumide according to claim 5 in crystalline particle form, having an average particle size value $(D_{50})$ of between 80 and 100 µm.

7. Dexloxiglumide in crystalline particle form according to claim 5, having a particle-size distribution with a span index of less than 2.5.

8. Dexloxiglumide according to claim 5, obtainable by means of a method of preparation by crystallization.

9. A pharmaceutical composition for oral use comprising, as active substance, dexioxiglumide according to claim 5.

10. A pharmaceutical composition according to claim 9, comprising dexioxiglumide in a quantity of between 50 and 500 mg and optional pharmaceutically acceptable vehicles.

11. A pharmaceutical composition according to claim 10, comprising, as inactive ingredients, pharmaceutically acceptable vehicles selected from diluents, disaggregants, lubricants, flow-promoting agents, and mixtures thereof.

12. A pharmaceutical composition according to claim 11, comprising, as vehicles, substances selected from the group which consists of starch, microcrystalline cellulose, sodium glycolate, talc, magnesium stearate, silicon dioxide, and mixtures thereof.

13. A method for preparing a pharmaceutical tablet including crystalline dexioxiglumide by compressing a powder comprising eccipients and crystalline dexloxiglumide, wherein crystalline dexloxiglumide is in a crystalline particle form having a percentage by volume of less than 15% of fine particles having a dimension less than 10 µm, and an average particle size value $(D_{50})$ between 50 and 130, and is prepared by crystallization of the crude product from solvent, wherein isopropyl ether is used as solvent, and the crystallization step is performed by adding a seeding of microcrystalline dexloxiglumide having an average particle size $(D_{50}) \leqq 20$ µm to a supersaturated solution of crude dexloxiglumide.

* * * * *